US00PP22679P2

(12) United States Plant Patent
Kivistik

(10) Patent No.: US PP22,679 P2
(45) Date of Patent: Apr. 24, 2012

(54) *CLEMATIS* PLANT NAMED 'UNAI 002'

(50) Latin Name: *Clematis jackmanii*
Varietal Denomination: UNAI 002

(76) Inventor: Aili Kivistik, Kose Parish (EE)

( * ) Notice: Subject to any disclaimer, the term of this patent is extended or adjusted under 35 U.S.C. 154(b) by 0 days.

(21) Appl. No.: 12/927,363

(22) Filed: Nov. 12, 2010

(51) Int. Cl.
*A01H 5/00* (2006.01)

(52) U.S. Cl. ..... Plt./228
(58) Field of Classification Search ..... Plt./228
See application file for complete search history.

*Primary Examiner* — Kent L Bell

(57) ABSTRACT

A new and distinct *Clematis* cultivar named 'UNAI 002' is disclosed, characterized by good resistance to normal diseases and pests of *Clematis*, continuous flowering from May through September, with flower buds continuously produced from the leaf axils. Plants are exceptionally floriferous with strong Red-Purple flowers. The new cultivar is a *Clematis*, suitable for ornamental garden purposes.

2 Drawing Sheets

Figure 1:
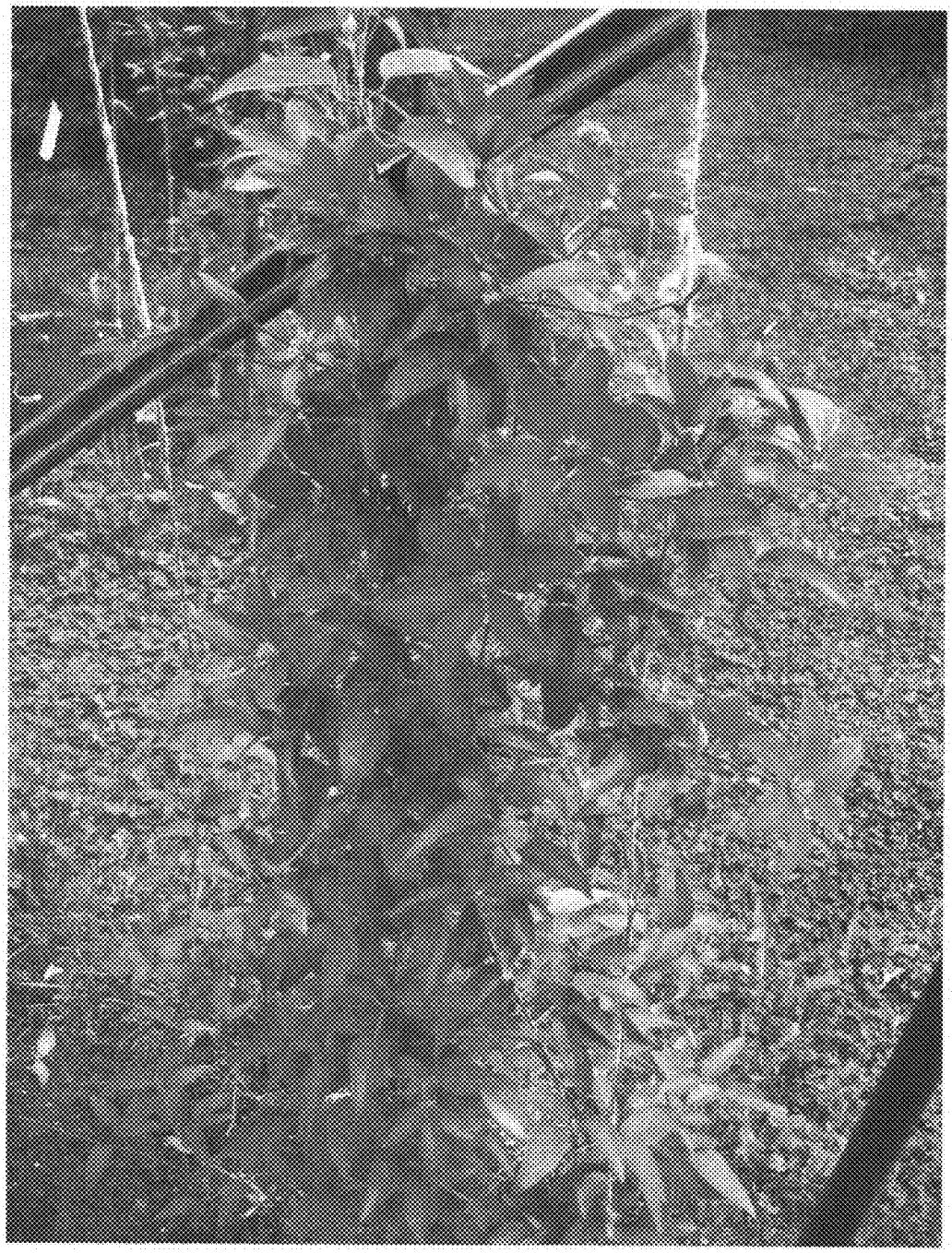

Latin name of the genus and species: *Clematis jackmanii.*
Variety denomination: 'UNAI 002'.

BACKGROUND OF THE INVENTION

The new cultivar is a product of a planned breeding program conducted by the inventor that began in 1978. The objective of the breeding program was to develop *Clematis jackmanii* varieties with abundant, continuous, long season flowering, with a good resistance to diseases and pests typical of *Clematis*. In 1982 the inventor, Aili Kivistik a citizen of Estonia, organized a group of unnamed, unpatented *Clematis jackmanii* varieties for an open pollination breeding project. Seeds originating from this open pollination were planted out, and the new variety was selected in 1984. Specific parents of the new variety are unknown, as the seed was bulk collected, without noting the variety collected from. All work was conducted at a non-commercial nursery in Roogoja, Estonia.

In 1988 the inventor first propagated 'UNAI 002' by vegetative cuttings at the same non-commercial nursery in Roogoja, Estonia. Subsequent generations have shown that the unique features of this cultivar are stable and reproduced true to type.

SUMMARY OF THE INVENTION

The cultivar 'UNAI 002' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'UNAI 002'. These characteristics in combination distinguish 'UNAI 002' as a new and distinct *Clematis* cultivar:

1. Good resistance to diseases and pests common to *Clematis.*
2. Continuous flowering from May through September.
3. Very floriferous plants.
4. Flower buds produced continuously from the leaf axils.
5. Strong Red-Purple colored flowers.

COMPARISON TO KNOWN VARIETIES

Plants of the new cultivar 'UNAI 002' are similar to known forms of *Clematis jackmanii* in most horticultural characteristics, however, plants of the new cultivar 'UNAI 002' produce flowers with larger, and more tepals than common forms of *Clematis jackmanii* known to the inventor. Additionally, plants of 'UNAI 002' flower continuously from May through September, whereas many known forms of *Clematis jackmanii* flower reliably 2 months only. The new variety also produces Red-Purple flowers, whereas the known varieties of *Clematis jackmanii* typically have Purple, or Violet-Blue flowers.

The new cultivar 'UNAI 002' can also be compared to the known variety *Clematis jackmanii* 'Superba'. Plants are similar in most horticultural characteristics, however, plants of the new cultivar produces flowers with 6 tepals, compared to 4 tepals on *Clematis jackmanii* 'Superba'. Additionally the new cultivar begins blooming one month earlier, and have a different tepal color.

The new cultivar 'UNAI 002' can also be compared to the known variety *Clematis jackmanii* 'Tie Dye' U.S. Plant Pat. No. 18,913. Plants are similar in most horticultural characteristics, however, plants of the new cultivar produces flowers that are larger, with more tepals, of a different color. Additionally the new cultivar begins blooming one month earlier, and flowers one month later than 'Tie Dye'.

BRIEF DESCRIPTION OF THE PHOTOGRAPHS

The accompanying photograph in FIG. 1 illustrates in full color a typical plant of 'UNAI 002'.

Figure 2:
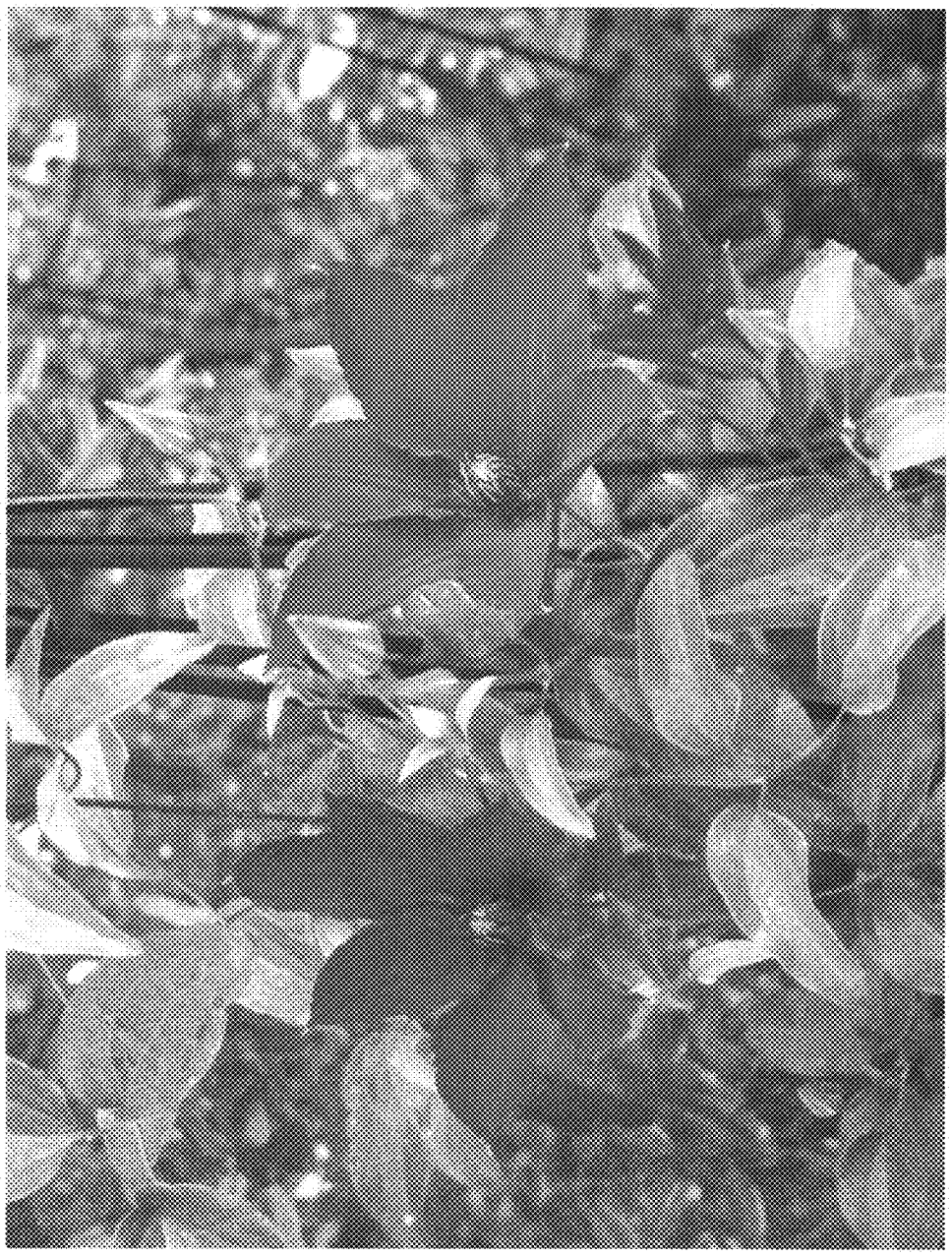

FIG. 2 shows a close up of a typical flower of 'UNAI 002' grown outdoors in Estonia. The plant is less than one year old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'UNAI 002' plants grown outdoors in Roogoja, Estonia. Plants are approximately 1 year old, in a 1 liter nursery container. The growing conditions are outdoors and unshaded. Temperatures ranged from approximately −2° C. to 20° C. at night to 5° C. to 35° C. during the day. Measurements and numerical values represent averages of typical plant types.

Botanical classification: *Clematis jackmanii* 'UNAI 002'

PROPAGATION

Time to rooting:

*Initiation.*—Approximately 40 days in the Summer at approximately 25° C.

*Rooted cuttings production.*—Approximately 40 days in the Summer at approximately 25° C.

Root description: Fine, fibrous.

PLANT

Growth habit: Climbing vine.

Height: Approximately 180 cm, measured from the soil line of the pot.

Plant spread: Approximately 80 cm when trained as a vine. Left untrained, approximately 100 cm.

Growth rate: Rapid. During active growing season in Spring, approximately 70 cm per month.

Branching characteristics: Very well branched, one main branch with at least 10 lateral branches.

Length of main stem: Approximately 180 cm.

Diameter of main stem: Approximately 0.2 to 0.5 cm.

Main stem color: Near RHS Brown 200B.

Main stem texture: Glabrous.

Internode length: Varies from 10 to 15 cm.

Strength: Strong, flexible, semi-woody.

FOLIAGE

Leaf:

*Type.*—Ternate leaves arranged opposite.

*Description ternate leaves.*—Leaves per lateral Branch: Approximately 60 leaflets. Average Length: Approximately 15 cm. Average Width: Approximately 10 cm. Leaflet Petiole: Average Length: Approximately 1.2 cm. Color: Near RHS Green 136A. Diameter: Approximately 0.2 cm. Texture: Glabrous.

*Leaflets.*—Average Length: Approximately 8 cm. Average Width: Approximately 4 cm. Shape of blade: Lanceolate. Apex: Acute. Base: Cordate or obtuse. Both bases found on plant. Attachment: Petioled. Margin: Entire. Texture of top surface: Smooth. Texture of bottom surface: Smooth. Leaf internode length: Approximately 1.5 cm. Resistance to stress and breakage: Very resistant to environmental and mechanical stress. Color: Young foliage upper side: Near RHS Green 136C. Young foliage under side: Near RHS Green 137D. Mature foliage upper side: Near RHS Green 136A Mature foliage under side: Near RHS Green 137C.

*Venation.*—Type: Pinnate. Venation color upper side: Near RHS Green 136A. Venation color under side: Near RHS Green 137C.

*Petiole.*—Average Length: Approximately 6 cm. Color: Near RHS Green 136A. Diameter: Approximately 0.2 cm. Texture: Glabrous.

Tendrils: Not present.

FLOWER

Bloom period:

*Natural season.*—Continuously from approximately May through September.

Flower type and habit: Single, axillary; flowers facing outward.

Flower longevity on plant: Approximately 5 days, after fully opened. Self-cleaning.

Quantity of flowers: Very free, continuous flowering. Mature plants have at least 50 open flowers during the flowering season.

Flower size:

*Diameter.*—Approximately 15 cm.

*Depth.*—Approximately 1 cm.

Corolla:

*Tepal arrangement.*—Single whorl.

*Quantity.*—Approximately 6 per flower.

*Size.*—Length: Approximately 7 cm. Width: Approximately 3.5 cm.

*Shape.*—Narrow deltoid.

*Margin.*—Entire.

*Apex.*—Acute.

*Base.*—Truncate.

*Aspect.*—Moderately concave. Margins slightly upturned on immature blooms. Margins slightly undulating on mature flowers.

*Texture.*—Smooth, velvety.

Color:

*Tepals.*—When opening: Upper surface: Near RHS Red-Purple 61A. Lower surface: Near RHS Red-Purple 71A. Fully opened: Upper surface: Near RHS Red-Purple 61A with flushes near N74A. Lower surface: Near RHS Red-Purple 71A. Ageing: Upper Surface: Near RHS Red-Purple 71A. Lower surface: Near RHS Red-Purple 71A.

Bud:

*Shape.*—Ovate.

*Length.*—Approximately 2 cm.

*Diameter.*—Approximately 1 cm.

*Color.*—Mainly Near RHS Grey-Green 192D.

Peduncles:

*Length.*—Approximately 6 cm.

*Width.*—Approximately 0.3 cm.

*Angle.*—Average 45°.

*Strength.*—Moderate.

*Color.*—Near RHS Green 138A.

Fragrance: None.

REPRODUCTIVE ORGANS

Stamens:

*Number.*—Approximately 60 per flower.

*Anther length.*—0.4 cm.

*Anther color.*—Near RHS Purple N77A.

*Anther shape.*—Oblong.

*Pollen quantity.*—Moderate.

*Pollen color.*—Near RHS Yellow-White 158D.

*Filament length.*—Approximately 0.6 cm.

*Filament aspect.*—Straight to slightly outwardly curved.

*Filament color.*—Near RHS Purple 76D.

Pistil:

*Number.*—Approximately 30 per flower.
*Length.*—Approximately 1.2 cm.
*Style color.*—Near RHS Purple 76D.
*Style length.*—Approximately 1.5 cm.
*Stigma.*—Shape: Linear. Color: Near RHS Yellow 11C.

OTHER CHARACTERISTICS

Seeds: Per flower, typically 30 round seeds, approximately 0.15 diameter. Colored near RHS Green 137B.

Disease/pest resistance: Very good resistance to pathogens and pests common to *Clematis* have been observed.

Temperature tolerance: Observed to tolerate temperatures from approximately −5° C. to at least 35° C.

What is claimed is:

1. A new and distinct cultivar of *Clematis* plant named 'UNAI 002' as herein illustrated and described.

* * * * *